(12) United States Patent
Mueller et al.

(10) Patent No.: US 6,790,981 B2
(45) Date of Patent: Sep. 14, 2004

(54) PROCESS FOR THE PREPARATION OF ACYLOXYBENZENESULFONATES

(75) Inventors: Wolf-Dieter Mueller, Charlotte, NC (US); Peter Naumann, Taunusstein (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 10/319,910

(22) Filed: Dec. 13, 2002

(65) Prior Publication Data

US 2004/0116725 A1 Jun. 17, 2004

(51) Int. Cl.$^7$ .............................................. C07C 69/017
(52) U.S. Cl. ...................................... 560/142; 560/130
(58) Field of Search ............................ 560/1, 129, 130, 560/142; 554/90

(56) References Cited

U.S. PATENT DOCUMENTS

| | | | |
|---|---|---|---|
| 3,503,888 A | 3/1970 | Miller et al. ................. | 252/117 |
| 4,537,724 A | 8/1985 | McKinnie et al. ........... | 260/400 |
| 4,544,503 A | 10/1985 | Berry ........................... | 260/402 |
| 4,587,054 A | 5/1986 | Hardy et al. ................. | 260/410.5 |
| 4,588,531 A | 5/1986 | Balzer et al. ................. | 260/402 |
| 4,588,532 A | 5/1986 | Moyne et al. ................. | 260/402 |
| 4,588,533 A | 5/1986 | Berry, Jr. ...................... | 260/402 |
| 4,619,779 A | 10/1986 | Hardy .......................... | 252/91 |
| 4,666,636 A | 5/1987 | Shen ....................... | 260/512 R |
| 4,693,848 A | 9/1987 | Balzer et al. ................. | 260/402 |
| 4,695,412 A | 9/1987 | Balzer et al. ........... | 260/507 R |
| 4,704,236 A | 11/1987 | Sankey et al. ................ | 260/402 |
| 4,705,649 A | 11/1987 | Balzer et al. ................. | 260/402 |
| 4,778,629 A | 10/1988 | Grabley et al. .............. | 260/402 |
| 4,788,316 A | 11/1988 | Thornthwaite et al. ..... | 558/268 |
| 4,803,015 A | 2/1989 | Wellbrock et al. .......... | 260/402 |
| 4,867,916 A | 9/1989 | Sanderson et al. .......... | 260/402 |
| 4,883,612 A | 11/1989 | Moyne et al. ............... | 260/402 |
| 4,908,474 A | 3/1990 | Sankey et al. ............... | 560/109 |
| 4,985,180 A | 1/1991 | Bellis et al. ................. | 260/404 |
| 5,069,828 A | 12/1991 | Dumas et al. ............... | 260/402 |
| 5,100,588 A | 3/1992 | Grabley et al. ............. | 260/402 |
| 5,274,172 A | 12/1993 | Chou et al. .................. | 560/109 |
| 5,606,104 A | 2/1997 | Hatayama et al. .......... | 560/221 |
| 5,710,296 A | 1/1998 | Foland et al. ................ | 554/167 |
| 5,795,854 A | 8/1998 | Angell et al. ................ | 510/312 |
| 6,448,431 B1 | 9/2002 | Hembre ....................... | 560/130 |
| 6,639,096 B2 * | 10/2003 | Reinhardt et al. .......... | 560/142 |

FOREIGN PATENT DOCUMENTS

| | | |
|---|---|---|
| EP | 0 148 148 | 7/1985 |
| EP | 0 153 223 | 8/1985 |
| EP | 0 164 786 | 12/1985 |
| EP | 0 165 480 | 12/1985 |
| EP | 0 220 826 | 5/1987 |
| JP | 08176092 | * 7/1996 |

OTHER PUBLICATIONS

CA:42:23143 abs of Journal of the Society of Chemical Industry, London Trans. and Comm by Hands et al 67 pp66–9 1948.*
CA:65:73204 abs of BE 670307 Nov. 1966.*
CA:55:2531 abs of GB 840009 Jul. 1960.*
CA:115:185811 abs of JP 03109499 May 1991.*

* cited by examiner

*Primary Examiner*—Jean F. Vollano
(74) *Attorney, Agent, or Firm*—Richard P. Silverman

(57) ABSTRACT

The invention relates to a process for the preparation of acyloxybenzenesulfonates starting from carbonyl halides and salts of phenolsulfonic acid which have a low water content. Surprisingly, it was discovered that acyloxybenzenesulfonates can be prepared in high yields and good grades, irrespective of the grade or reactivity of the phenolsulfonic acid derivative, if the reaction of the phenolsulfonic acid with an alkanecarboxylic acid derivative is carried out in an aliphatic or aromatic solvent in the presence of 0.5 to 25% by weight of a polyglycol ether.

22 Claims, 1 Drawing Sheet

PROCESS FOR THE PREPARATION OF ACYLOXYBENZENESULFONATES

The invention relates to a process for the preparation of acyloxybenzenesulfonates starting from carbonyl halides and salts of phenolsulfonic acid which have a low water content.

BACKGROUND OF THE INVENTION

Acyloxybenzenesulfonic acids and their salts are compounds which have been known for a long time. Depending on the chain length of the acyl group, they can be used as surfactants, bleach activators or in other applications. These compounds may be obtained by reacting sodium phenolsulfonate (SPS) with the chloride of an organic carboxylic acid. The reaction medium used is organic solvents such as methylene chloride (U.S. Pat. No. 3,503,888), high-boiling hydrocarbons (U.S. Pat. No. 4,704,236; EP 220 826), xylene or toluene (EP 164 786). According to U.S. Pat. No. 5,069,828, this reaction is carried out in an aprotic organic solvent in the presence of a phase transfer catalyst.

U.S. Pat. No. 6,448,431 (WO 01/19 771) describes the reaction of acyl chlorides with SPS in trifluoroacetic acid (TFA) as solvent. In the examples, the ratio of TFA:SPS used is from 0.5:1 to 3:1. The high cost of TFA, its complete removal from the reaction mixture, and possible transesterification reactions or the formation of byproducts, however, prevents the utilization of the process on an industrial scale.

All of the processes have the problem that virtually anhydrous SPS must be used for the reaction since otherwise acyl halide or the finished ester are hydrolyzed in the presence of water, which leads to considerable losses in yield. SPS is available commercially as dihydrate with a water content of about 15%. Conventional drying can reduce the water content to about 2%. According to U.S. Pat. No. 5,069,828, it is possible to remove the remaining amount of water by azeotropic distillation in the presence of an entrainer such as xylene. However, due to the high time requirement, this is of little use in plants which operate continuously. Alternatively, the water content can be reduced to less than 1% by drying in an inert or vacuum atmosphere by techniques well known to those skilled in the art. However, as is known from U.S. Pat. No. 4,666,636, which is hereby incorporated by reference, that certain drying conditions must be observed exactly in order to maintain the reactivity of the SPS. If those drying conditions are not followed, SPS can participate in a number of secondary reactions, as a result of which both the degree of conversion of the subsequent acylation, and also the color of the end products is significantly impaired. Over drying of the SPS leads to degrees of conversion of less than 50% in the subsequent acylation reaction.

To solve this problem it is recommended in DE 101 39 663.5 (U.S. application Ser. No. 10/209,723, filed Aug. 1, 2002) to add nitrogen containing compounds such as DMF or NMP. This increases the degree of conversion, but problems arise regarding the filtration of the reaction mixture. In addition problems arise with malodor.

It is therefore an object of the present invention to develop a process which can be carried out industrially and also continuously, which leads, in very good yields, to the most uniform products possible which, with regard to composition, grade and color, are suitable for use in laundry detergents and cleaners. In this connection, the process should be independent of the grade of the sodium phenolsulfonate used and its pretreatment.

SUMMARY OF THE INVENTION

Surprisingly, it has now been found that acyloxybenzenesulfonates can be prepared in high yields and good grades, irrespective of the relative reactivity or grade of the SPS used, if the reaction of the SPS with an alkanecarboxylic acid derivative is carried out in an aliphatic or aromatic solvent in the presence of 0.5 to 25% by weight of a polyglycol ether.

In one embodiment, invention relates to a process for the preparation of acyloxybenzenesulfonates by reaction of phenolsulfonates which have a water content of less than 0.5% by weight, preferably less than 0.2% by weight, of water with alkanecarboxylic acid derivatives in an aliphatic or aromatic hydrocarbon, which comprises carrying out the reaction in the presence of from 0.5 to 25% by weight of a polyglycol ether of the formula

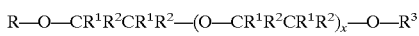

wherein R and $R^3$ are $C_1$ to $C_4$ alkyl, $R^1$ and $R^2$ are hydrogen or $C_1$ to $C_2$ alkyl and x is a number from 1 to 4.

In another embodiment, the invention relates to a process for the continuous production of acyloxybenzenesulfonate. The continuous process comprises passing a phenolsulfonate compound, which has a water content of less than 0.5, and an alkanecarboxylic acid derivative to a continuous reaction zone. The continuous reaction zone contains a mother liquor comprising an aliphatic or aromatic hydrocarbon, in the presence of from 0.5 to 25 weight % of a polyglycol ether to provide a reaction mixture. At effective conditions, the reaction mixture is reacted to provide a crude acyloxybenzenesulfonate. The crude acyloxybenzenesulfonate from the mother liquor; and at least a first portion of the mother liquor is returned to the continuous reaction zone. In the continuous reaction zone during the reaction step, at least a portion of the water reacts with the alkanecarboxylic acid derivative to form impurities. In order to minimize the buildup of the impurities in the mother liquor, a second portion of the mother liquor is regenerated to remove at least a portion of the impurities. A regenerated mother liquor is returned to the continuous reaction zone.

DETAILED DESCRIPTION OF THE INVENTION

Figure 1:
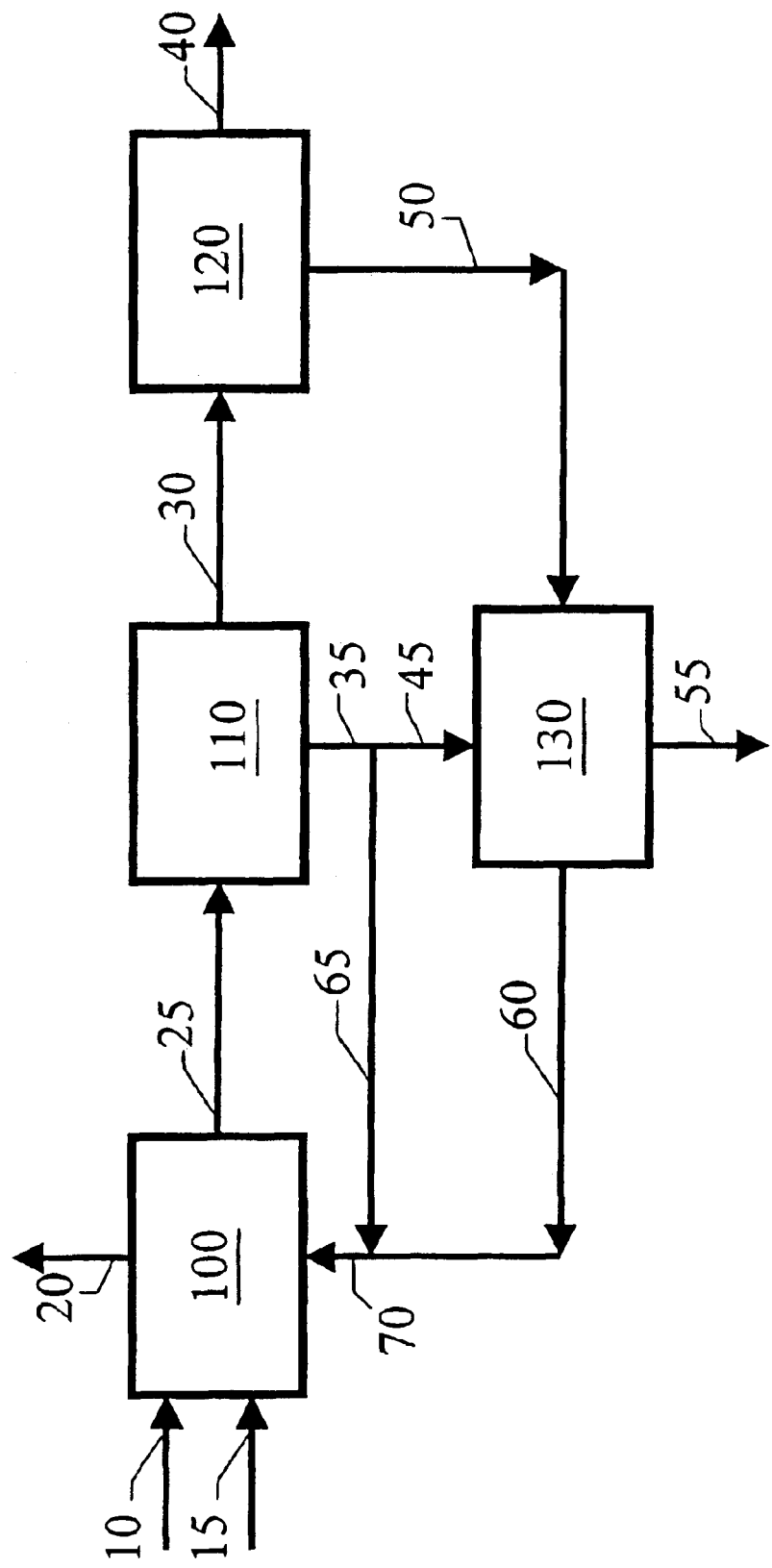
FIG. 1 is a simplified flow diagram of the process of the present invention.

The phenolsulfonates used as starting compounds are preferably compounds of the formula

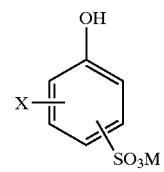

where X is hydrogen, halogen or $C_1$–$C_4$-alkyl and M is an alkali metal ion or alkaline earth metal ion.

Preference is given to sodium ortho- or para-phenolsulfonates, in particular sodium para-phenolsulfonate (SPS), which may comprise 0 to 20% of the corresponding ortho isomers as a result of the preparation. More preferably, sodium para-phenolsulfonate (SPS), comprises 0.05 to 5% of the corresponding ortho isomers.

SPS is available commercially as dihydrate, i.e. with a water content of 15%. For the inventive reaction with an alkanecarboxylic acid derivative, the phenolsulfonate must firstly be dried to a residual moisture of at most 0.5% by weight, preferably at most 0.2% by weight, of water. This can be carried out by customary methods known per se, for example in a disc drier, which permits drying to a residual moisture of less than 0.1% by weight.

The drying times may be between 1 min and 18 h depending on the equipment used, the temperatures may be between 80 and 250° C. In the process according to the invention, the quality of the dried SPS has no influence on the yield of the acylation reaction and, on average, it is possible to attain conversions greater than 95%. In particular, it is also possible to apply drying conditions which lie outside of the optimum drying conditions specified in U.S. Pat. No. 4,666,636, i.e. those which lead to "overdried" product. According to the prior art, such a product cannot be used for acylation reactions since it is not reactive enough.

The alkanecarboxylic acid derivatives which may be used are either the halides or the anhydrides. In particular, the carbonyl chlorides or bromides are suitable, preference being given to the chlorides. These can be prepared from the corresponding carboxylic acids, e.g. by reaction with phosgene, thionyl chloride, phosphorus trichloride, phosphorus oxychloride, phosphorus pentachloride or phosphorus tribromide. In the case of the anhydrides, it is possible to use symmetrical or asymmetrical compounds. Examples thereof are nonanoic anhydride, octanoic anhydride or acetylnonanoic anhydride.

The carboxylic acids which may be used are linear or branched, saturated or unsaturated alkanecarboxylic acids having 6 to 22 carbon atoms. Examples thereof are hexanoic acid, heptanoic acid, octanoic acid, methyloctanoic acid, nonanoic acid, 3,3,5-isononanoic acid, decanoic acid, undecanoic acid, undecenoic acid, lauric acid, myristic acid, hydrogenated tallow fatty acid and stearic acid. Particular preference is given to octanoic acid, nonanoic acid, isononanoic acid, decanoic acid and lauric acid. The alkanecarboxylic acid can carry further substituents, such as halogens, nitro groups or amino groups.

According to the invention, carboxylic acid derivative and phenolsulfonate can preferably be reacted together in the molar ratio from 0.9:1 to 2:1, preferably 1:1 to 1.5:1.

The reaction media used are aliphatic or aromatic hydrocarbons having boiling points between 80 and 220° C., in particular 100 to 180° C., e.g. toluene, xylene, paraffins having 8 to 22 carbon atoms, such as decane, undecane, dodecane, hexadecane or octadecane or mixtures thereof. Particularly suitable media are aliphatic hydrocarbon mixtures of de-aromatized isoparaffins as are commercially available as Shellsols (Available from Shell Chemical LP, Houston, Tex.), ISOPAR G and ISOPAR 4 (Available from ExxonMobil Chemical, Houston, Tex.). The solubility of the SPS in this reaction medium is generally less than 1%.

Prior to starting the reaction a polyglycol ether is added as defined by the general formula above. In this formula R and $R^3$ or $R^1$ and $R^4$ may by the same or different. Preferred are those polyglycol ethers wherein the group $CR^1R^2CR^1R^2$ is $C_2H_4$ or $C_3H_5$.

Polyethyleneglycol ethers are preferred which have a boiling point between 130° C. and 300° C. Especially preferred are diethyleneglycol-dimethylether, diethyleneglycol-diethylether, diethyleneglycol-ethylmethylether, diethyleneglycol-dibutylether and dipropyleneglycol-dimethylether.

The polyglycol ether is used in an amount of 0.5 to 25% by weight, preferably 1 to 20%, based on the amount of the solvent used; and most preferably the polyglycol ether is used in an amount of 3 to 15%, based on the amount of the solvent used.

The acylation reaction is carried out at temperatures between 60 and 200° C., in particular between 100 and 150° C. The gas which forms during the reaction is withdrawn, and the reaction is optionally blanketed with a stream of inert gas comprising nitrogen or argon. The reaction is carried out as a heterogeneous reaction (slurry) since neither the phenolsulfonate nor the acyloxybenzenesulfonate which forms has a noteworthy solubility in the reaction medium. The acylation reaction time depends on the reaction conditions and may be between 10 min and 5 hours, preferably the acylation reaction time ranges from 30 to 120 min.

In a particular embodiment, the acylation reaction according to the invention can be carried out continuously. For this purpose, reactor cascades or tubular reactors, as are known to the person skilled in the art, are particularly suitable.

When the acylation reaction is complete, the reaction product is isolated by means of conventional separation methods. Suitable for this purpose are centrifuges, filtration, and other separation equipment well-known to those skilled in the art. The mother liquor can be used or circulated for the subsequent reactions without further purification. The acyloxybenzenesulfonate formed is produced in high yields in the form of a white powder which can be isolated by conventional drying.

The acyloxybenzenesulfonate obtained in this way can be used as surfactant or persalt activator in laundry detergents and cleaners, such as pulverulent heavy-duty detergents, stain-removal salts or pulverulent machine dishwashing detergents. To increase the storage stability in these formulations, it can be converted into a granular form, as is known to the person skilled in the art.

DETAILED DESCRIPTION OF THE DRAWING

The process of the present invention is hereinafter described with reference to FIG. 1 which illustrates various aspects of the process. It is to be understood that no limitation to the scope of the claims which follow is intended by the following description. Those skilled in the art will recognize that these process flow diagram has been simplified by the elimination of many necessary pieces of process equipment including some heat exchangers, process control systems, pumps, filtration systems, etc. It may also be discerned that the process flow depicted in the Figure may be modified in many aspects without departing from the basic overall concept of the invention.

FIG. 1 illustrates one embodiment of the present invention which comprises the continuous production of acyloxybenzenesulfonate. Referring to FIG. 1, a phenolsulfonate compound, which has a water content of less than 0.5%, in line 10 is passed to a continuous reaction zone 100 comprising at least one stirred reactor. An alkanecarboxylic acid derivative in line 15 is passed to the continuous reaction zone 100. The continuous reaction zone 100 contains a mother liquor which comprises an aliphatic or aromatic hydrocarbon, in the presence of from 0.5 to 25 weight % of a polyglycol ether to provide a reaction mixture. The continuous reaction zone is raised to effective reaction conditions, and the reaction mixture is reacted to provide a crude acyloxybenzenesulfonate. In the continuous reaction zone 100 during the reaction step, at least a portion of the water reacts with the alkanecarboxylic acid derivative to form impurities such as the alkanecarboxylic acid and the alkanecarboxylic acid anhydride. If the alkanecarboxylic acid derivative is a salt, any gas generated by the reaction in the continuous reaction zone is removed in line 20 for recovery or disposal by techniques well known to those skilled in the art. A continuous reaction zone effluent in line 25 comprising the crude acyloxybenzenesulfonate and mother liquor is removed from the continuous reaction zone 100 and passed to a recovery zone 110. The recovery of the crude acyloxybenzenesulfonate from the mother liquor can be performed by filtration or centrifuging. Additional washing steps can be performed in the recovery zone 110 as required. In the recovery zone 110, the crude acyloxybenzenesulfonate in line 30 is recovered from the mother liquor and the solid acyloxybenzenesulfonate is passed to a drying zone 120. In the drying zone, the solid acyloxybenzenesulfonate is dried. The dried acyloxybenzenesulfonate is recovered from the drying zone 120 in line 40. The dried acyloxybenzenesulfonate in line 40 can be further processed into flakes, extrudates, prills, or pellets. Any liquid recovered in the drying zone 120 is passed in line 50 to a regeneration zone 130. Mother liquor separated from the crude acyloxybenzenesulfonate is removed from the recovery zone 110 in line 35. At least a first portion of the mother liquor in line 35 is returned to the continuous reaction zone 100 via lines 35, 65 and 70. A second portion of the mother liquor in line 35 is passed to regeneration zone 130 in line 45. In the regeneration zone, mother liquor is regenerated to remove at least a portion of impurities before returning a regenerated mother liquor to the continuous reaction zone 100. Impurities removed from the mother liquor in the regeneration zone 130 are withdrawn in line 55. The impurities in line 55 are passed to a disposal zone (not shown).

EXAMPLES

Example 1a

Preparation of Anhydrous 4-phenolsulfonate sodium (Good Quality)

1 kg of 4-phenolsulfonate sodium with a water content of 2.6% were dried analogously to Example 1 from U.S. Pat. No. 4,666,636. This gave 975 g of 4-phenolsulfonate sodium with a water content of <0.1%.

Example 1b

Preparation of Anhydrous 4-phenolsulfonate sodium (Poor Quality)

1 kg of 4-phenolsulfonate sodium with a water content of 2.6% were dried for 12 h at 180° C. This gave 975 g of 4-phenolsulfonate sodium with a water content of <0.1%.

Comparative Example A

Use of SPS, dried in accordance with Example 1a 98.1 g (0.5 mol) of dried phenolsulfonate sodium, prepared according to Example 1, were introduced into 150 g of ISOPAR G and heated to 120° C. 114.8 g (0.65 mol) of nonanoyl chloride were added dropwise over the course of 30 min, and the mixture was after-stirred at 130° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Gross yield: 164.8 g (yield 98% weight) of a white powder with a nonanoyloxybenzenesulfonate sodium (NOBS) content of 98%. Net yield of pure NOBS: 96% by weight.

Comparative Example B

Use of Overdried SPS, According to Example 1b 98.1 g (0.5 mol) of dried phenolsulfonate sodium, prepared according to Example 2, were introduced into 150 g of ISOPAR G and heated to 120° C. 114.8 g (0.65 mol) of nonanoyl chloride were then added dropwise over the course of 30 min, and the mixture was after-stirred at 120° C. The HCl gas which formed during the reaction was withdrawn. The reaction mixture was cooled after 2 h to 80° C. and filtered through a filter. The gray reaction product was then washed twice with a small amount of ISOPAR G and then dried overnight in a drying cabinet at 110–130° C. Gross yield: 129.5 g (yield 77% weight) of a beige-brown powder with a nonanoyloxybenzenesulfonate sodium (NOBS) content of 59%. Net yield of pure NOBS: 45% by weight.

Example 2

98.1 g (0.5 mol) of dried phenolsulfonate sodium, prepared according to Example 1b, were introduced into 135 g of ISOPAR G and heated to 120° C. 15 g of diethyleneglycol-dimethylether were added. 114.8 g (0.65 mol) of nonanoyl chloride were then added dropwise over the course of 30 min, and the mixture was after-stirred at 120° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Gross yield: 165.1 g (yield 98.1% weight) of a white powder with a nonanoyloxybenzenesulfonate sodium (NOBS) content of 96.5%. Net yield of pure NOBS: 94.7% by weight. The mother liquor could be used for the subsequent batch without further purification.

Example 3

98.1 g (0.5 mol) of dried phenolsulfonate sodium, prepared according to Example 1b, were introduced into 143 g of ISOPAR G and heated to 130° C. 7 g of diethyleneglycol-diethylether were added. 114.8 g (0.65 mol) of nonanoyl chloride were then added dropwise over the course of 30 min, and the mixture was after-stirred at 130° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Gross yield: 161.8 g (yield 96.2% weight) of a white powder with a nonanoyloxybenzenesulfonate sodium (NOBS) content of 98.7%. Net yield of pure NOBS: 94.9% by weight.

Example 4

98.1 g (0.5 mol) of dried phenolsulfonate sodium, prepared according to Example 1b, were introduced into 140 g of ISOPAR G and heated to 120° C. 10 g of diethyleneglycol-dimethylether were added. 114.8 g (0.65 mol) of nonanoyl chloride were then added dropwise over the course of 30 min, and the mixture was after-stirred at 120° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Gross yield: 162.5 g (yield 97.1% weight) of a white powder with a nonanoyloxybenzenesulfonate sodium (NOBS) content of 98%. Net yield of pure NOBS: 95.2% by weight.

Example 5

98.1 g (0.5 mol) of dried phenolsulfonate sodium, prepared according to Example 1b, were introduced into 140 g of ISOPAR G and the mixture was heated to 110° C. 10 g of diethyleneglycol-dimethylether were added. 142 g (0.65 mol) of lauroyl chloride were then added dropwise over the course of 30 min and the mixture was after-stirred at 130° C. The HCl gas which formed during the reaction was withdrawn. The reaction mixture was cooled after 2 h to 80° C. and filtered through a filter. The white reaction product was then washed twice with a small amount of ISOPAR G and then dried overnight in a drying cabinet at 110–130° C. Gross yield: 181.8 g (yield 96.1% weight) of a white powder with a lauroyloxybenzenesulfonate sodium (LOBS) content of 98.2%. Net yield of pure LOBS: 94.3% by weight.

We claim:

1. A process for the production of acyloxybenzenesulfonate comprising reacting a phenolsulfonate, having a water content of less than 0.5, and an alkanecarboxylic acid derivative selected from the group consisting of a halide, an anhydride, and mixtures thereof of said alkanecarboxylic acid in an aliphatic or aromatic hydrocarbon, in the presence of from 0.5 to 25 weight % of a polyglycol ether of the formula

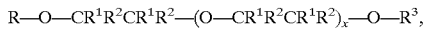

R—O—CR$^1$R$^2$CR$^1$R$^2$—(O—CR$^1$R$^2$CR$^1$R$^2$)$_x$—O—R$^3$, wherein R and R$^3$ are C$_1$–C$_4$ alkyl, and R$^1$ and R$^2$ are H or C$_1$–C$_2$ alkyl, and X is a number from 1 to 4.

2. The process of claim 1, wherein the phenolsulfonate is of the formula

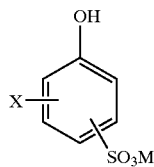

where X is hydrogen, halogen or C$_1$–C$_4$-alkyl and M is an alkali metal ion or alkaline earth metal ion.

3. The process of claim 1, wherein the phenolsulfonate is sodium phenolsulfonate.

4. The process of claim 1, wherein the alkanecarboxylic acid derivative is a C$_8$–C$_{22}$-carbonyl chloride or bromide.

5. The process of claim 1, wherein the alkanecarboxylic acid derivative is a C$_8$–C$_{22}$-carbonyl chloride.

6. The process of claim 1, wherein the alkanecarboxylic acid derivative is a halide or anhydride of the alkanecarboxylic acid selected from the group consisting of octanoic acid, nonanoic acid, isononanic acid, decanoic acid, lauric acid and mixtures thereof.

7. The process of claim 1, wherein a molar ratio of the alkanecarboxylic acid derivative to the phenolsulfonate ranges from 0.9:1 to 2:1.

8. The process of claim 1, wherein the water content of the phenolsulfonate is less than 0.2 weight percent.

9. The process of claim 1, wherein the polyglycol ether is present in an amount ranging from about 0.5 to about 15% by weight.

10. The process of claim 1, wherein the polyglycol ether is selected from the group consisting of diethyleneglycol-dimethylether, diethyleneglycol-diethylether, diethyleneglycol-ethyl-methylether, diethyleneglycol-dibutylether, dipropyleneglycol-dimethylether, and mixtures thereof.

11. The process of claim 1, wherein the polyglycol ether comprises diethyleneglycol-dimethylether.

12. A process for the production of acyloxybenzenesulfonate comprising a) combining a phenolsulfonate, having a water content of less than 0.5, and an alkanecarboxylic acid derivative selected from the group consisting of a halide, an anhydride, and mixtures thereof of said alkanecarboxylic acid in an aliphatic or aromatic hydrocarbon, in the presence of from 0.5 to 25 weight % of a polyglycol ether of the formula

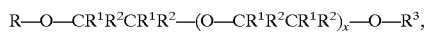

R—O—CR$^1$R$^2$CR$^1$R$^2$—(O—CR$^1$R$^2$CR$^1$R$^2$)$_x$—O—R$^3$, wherein R and R$^3$ are C$_1$–C$_4$ alkyl, and R$^1$ and R$^2$ are H or C$_1$–C$_2$ alkyl, and X is a number from 1 to 4 to provide a reaction mixture;

b) reacting the reaction mixture at an acylation reaction temperature ranging from 60 to 200° C., to produce a crude acyloxybenzenesulfonate; and, c) recovering the crude acyloxybenzenesulfonate.

13. The process of claim 12, further comprising washing the crude acyloxybenzenesulfonate to provide a washed acyloxybenzenesulfonate.

14. The process of claim 13, further comprising drying the washed acyloxybenzenesulfonate to provide a dried acyloxybenzenesulfonate.

15. The process of claim 14, further comprising forming the dried acyloxybenzenesulfonate into a granular product selected from extrudate, prills, pellets, and mixtures thereof.

16. A process for the continuous production of acyloxybenzenesulfonate, said process comprising:

a) passing a phenolsulfonate, having a water content of less than 0.5 and an alkanecarboxylic acid derivative selected from the group consisting of a halide, an anhydride, and mixtures thereof of said alkanecarboxylic acid to a continuous reaction zone containing a mother liquor comprising an aliphatic or aromatic hydrocarbon, in the presence of from 0.5 to 25 weight % of a polyglycol ether of the formula

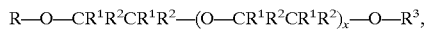

R—O—CR$^1$R$^2$CR$^1$R$^2$—(O—CR$^1$R$^2$CR$^1$R$^2$)$_x$—O—R$^3$, wherein R and R$^3$ are C$_1$–C$_4$ alkyl, and R$^1$ and R$^2$ are H or C$_1$–C$_2$ alkyl, and X is a number from 1 to 4 to provide a reaction mixture;

b) reacting the reaction mixture at effective conditions to provide a crude acyloxybenzenesulfonate;

c) recovering the crude acyloxybenzenesulfonate from the mother liquor; and, d) returning at least a first portion of the mother liquor to the continuous reaction zone.

17. The process of claim 16, wherein at least a portion of the water reacts with the alkanecarboxylic acid derivative to form impurities.

18. The process of claim 17, further comprising regenerating a second portion of the mother liquor to remove at least a portion of the impurities and returning a regenerated mother liquor to the continuous reaction zone.

19. The process of claim 9 wherein the reacting step is carried out for a reaction time ranging from 10 minutes to 5 hours.

20. The process of claim 12, wherein the recovering step comprises filtering or centrifuging.

21. The process of claim 1, wherein the phenolsulfonate comprises a para-phenolsulfonate and up to 20 wt-% ortho-phenolsulfonate.

22. The process of claim 13, wherein the crude acyloxy-benzenesulfonate is washed with an aliphatic or aromatic hydrocarbon.

* * * * *